US008556802B2

(12) United States Patent
Liu et al.

(10) Patent No.: US 8,556,802 B2
(45) Date of Patent: Oct. 15, 2013

(54) ENDOSCOPE AND MAGNETIC FIELD CONTROL METHOD THEREOF

(75) Inventors: Chih-Wen Liu, Taipei (TW); R-Shin Tzeng, Taipei (TW); Gi-Shih Lien, Taipei (TW)

(73) Assignee: National Taiwan University, Taipei (TW)

( * ) Notice: Subject to any disclaimer, the term of this patent is extended or adjusted under 35 U.S.C. 154(b) by 1272 days.

(21) Appl. No.: 12/166,232

(22) Filed: Jul. 1, 2008

(65) Prior Publication Data

US 2009/0012363 A1 Jan. 8, 2009

(30) Foreign Application Priority Data

Jul. 6, 2007 (TW) .............................. 96124653 A

(51) Int. Cl.
*A61B 1/00* (2006.01)
*A61B 1/04* (2006.01)
(52) U.S. Cl.
USPC ......................................... 600/118; 600/103
(58) Field of Classification Search
USPC .......................................... 600/109, 118, 160
See application file for complete search history.

(56) References Cited

U.S. PATENT DOCUMENTS

| 2003/0181788 A1* | 9/2003 | Yokoi et al. ................... 600/160 |
| 2004/0181127 A1* | 9/2004 | Matsumoto et al. .......... 600/101 |
| 2004/0236180 A1* | 11/2004 | Uchiyama et al. ............ 600/109 |
| 2005/0052178 A1* | 3/2005 | Ries ......................... 324/207.23 |
| 2005/0062562 A1* | 3/2005 | Ries .................................. 335/1 |
| 2005/0216231 A1* | 9/2005 | Aoki et al. ..................... 702/183 |
| 2006/0169293 A1* | 8/2006 | Yokoi et al. ................... 128/899 |
| 2006/0209185 A1* | 9/2006 | Yokoi ............................. 348/65 |
| 2007/0161862 A1* | 7/2007 | Yokoi et al. ................... 600/175 |
| 2007/0191671 A1* | 8/2007 | Kawano et al. ................. 600/12 |
| 2007/0270628 A1* | 11/2007 | Kawano et al. ................. 600/12 |
| 2008/0300453 A1* | 12/2008 | Aoki et al. ..................... 600/103 |
| 2008/0300458 A1* | 12/2008 | Kim et al. ...................... 600/118 |
| 2009/0231073 A1* | 9/2009 | Horisaka et al. ............... 335/209 |
| 2009/0318761 A1* | 12/2009 | Rabinovitz .................... 600/118 |
| 2010/0001592 A1* | 1/2010 | Kawano et al. ............. 310/12.14 |
| 2010/0022835 A1* | 1/2010 | Kimura et al. ................. 600/118 |
| 2010/0030026 A1* | 2/2010 | Uchiyama et al. ............. 600/118 |
| 2011/0184235 A1* | 7/2011 | Schostek et al. .............. 600/109 |

* cited by examiner

*Primary Examiner* — Philip R Smith
*Assistant Examiner* — William Chou

(57) ABSTRACT

An endoscope device is provided. The endoscope device includes a capsule sensor entering a human body for detection and sending a signal, a driving device movably disposed outside of the human body and moving and rotating the capsule sensor in the human body with non-contact force for omni-directional human body detection, a data receiving device disposed outside of the human body and receiving signals from the capsule sensor, and a power supply device providing power to the driving device and the data receiving device.

7 Claims, 12 Drawing Sheets

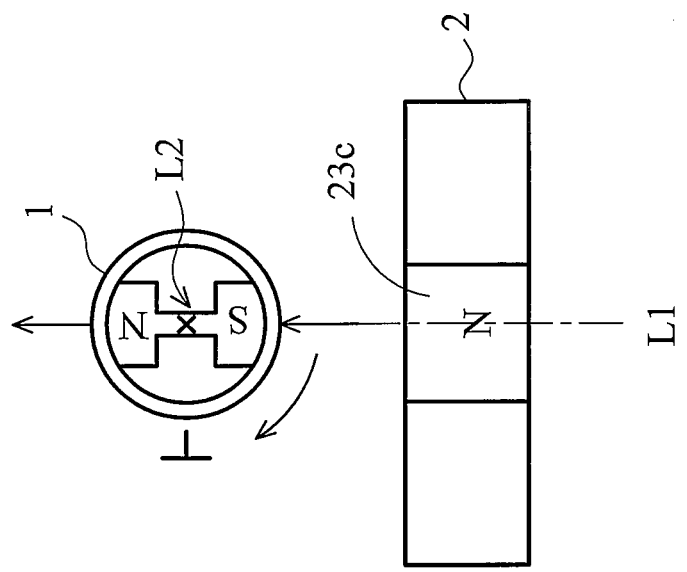
FIG. 4e2
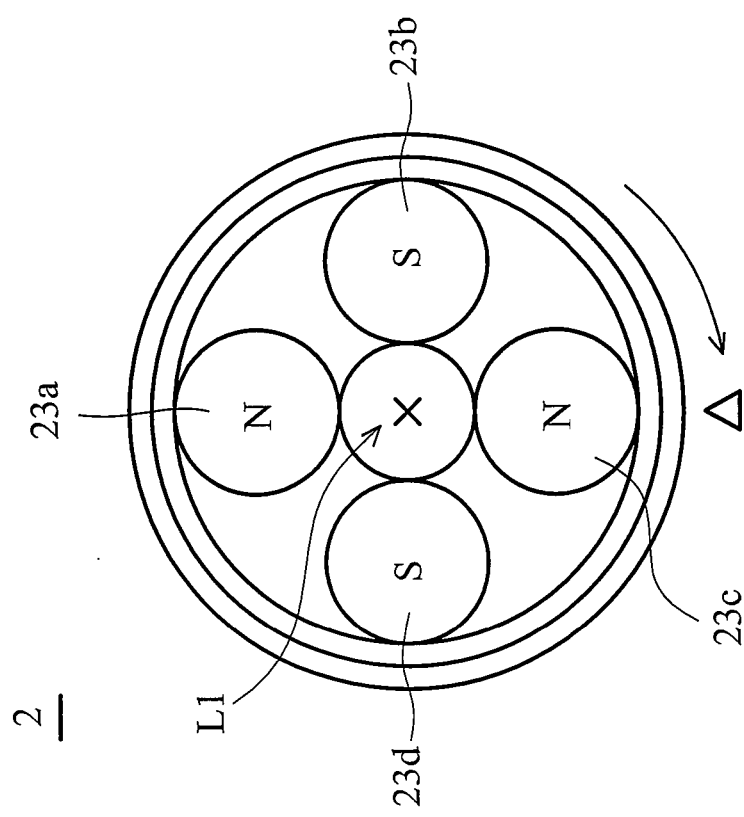
FIG. 4e1

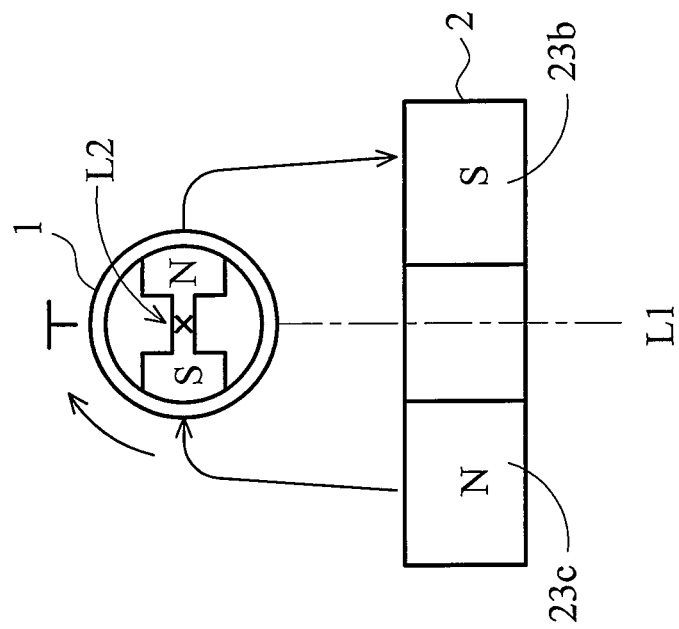
FIG. 4f2
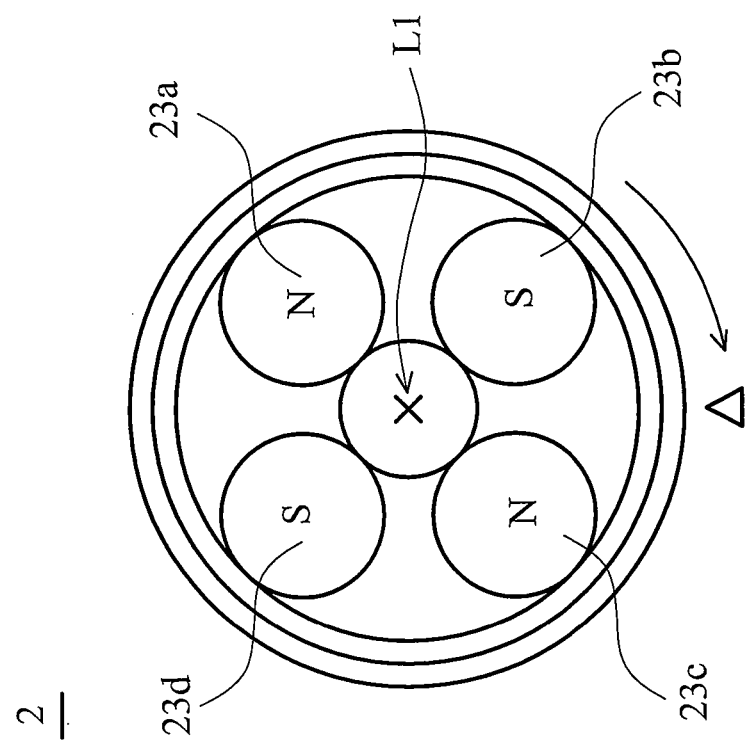
FIG. 4f1

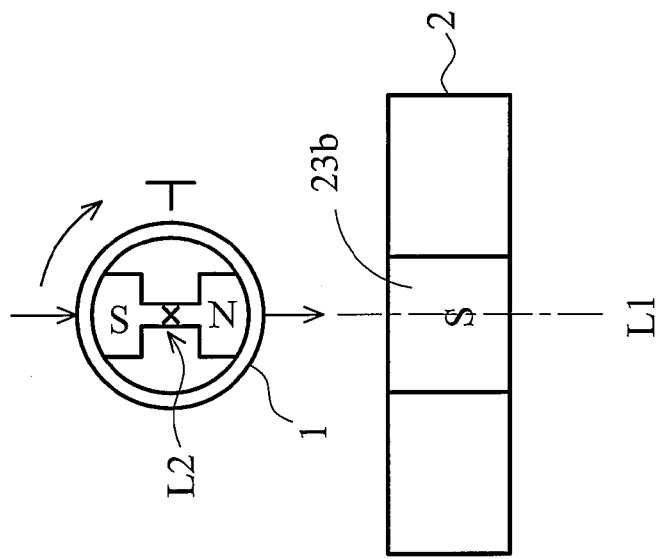
FIG. 4g2
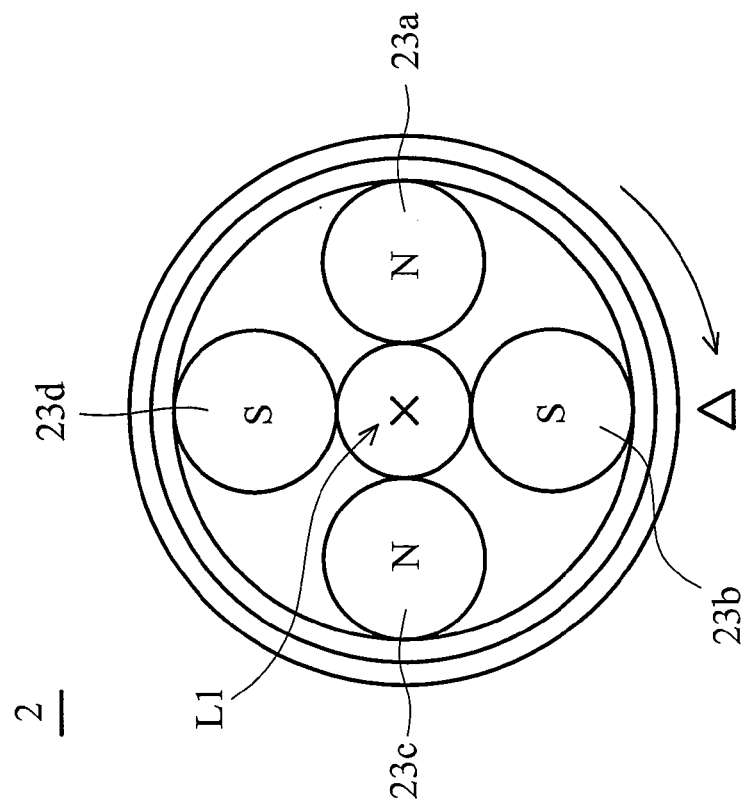
FIG. 4g1

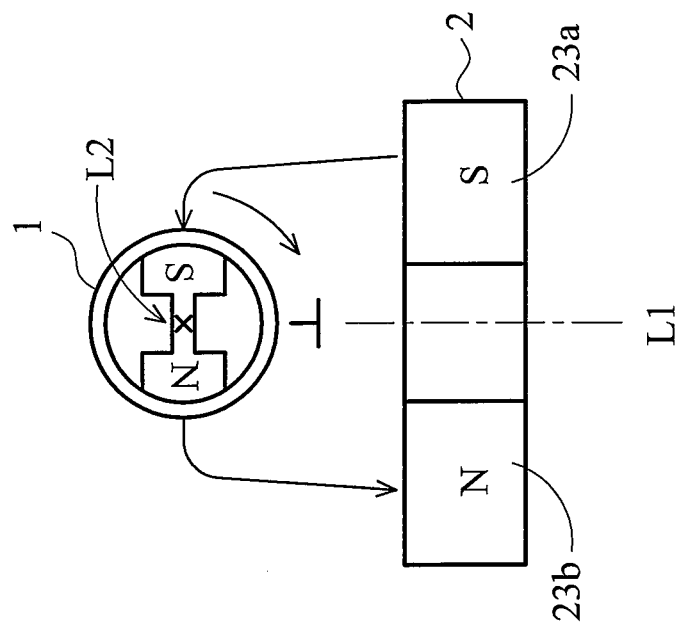
FIG. 4h2
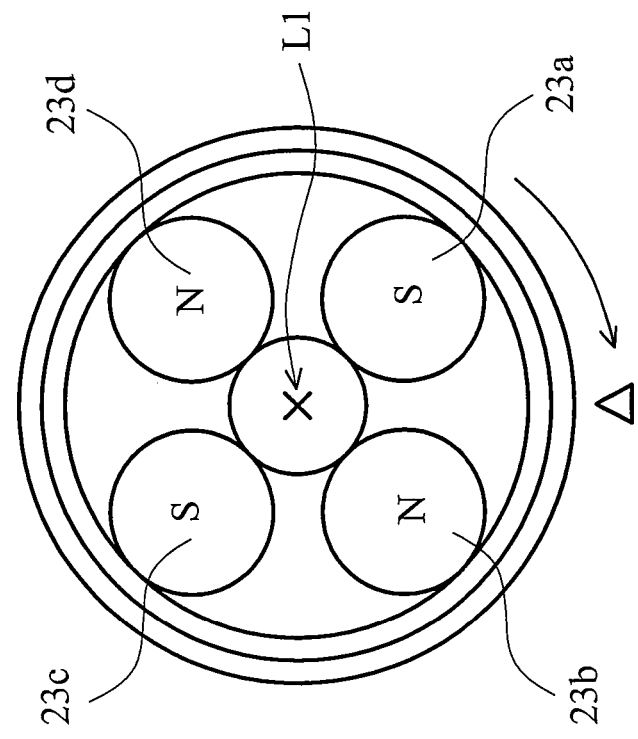
FIG. 4h1

ENDOSCOPE AND MAGNETIC FIELD CONTROL METHOD THEREOF

CROSS REFERENCE TO RELATED APPLICATIONS

This application claims priority of Taiwan Patent Application No. 96124653, filed on Jul. 6, 2007, the entirety of which is incorporated by reference herein.

BACKGROUND OF THE INVENTION

1. Field of the Invention

The invention relates to an endoscope, and in particular relates to a capsule-shaped endoscope that enters the human body for detection.

2. Description of the Related Art

For a conventional gastroscopy test, a hose with optical fibers and lenses is used to inspect the gullet, stomach, and duodenum. Doctors can clearly and precisely locate alimentary canal diseases using the test. Since the hose has a considerable diameter, when the hose enters the alimentary canal, the patient may feel afraid or uncomfortable. In addition, the gastroscopy test is not able to completely inspect small intestine areas.

The apparatus used for small intestine inspection is a capsule endoscope, such as a Given Imaging M2A produced in Israel. The capsule endoscope, Given Imaging M2A, as shown in FIG. 1, comprises a cover 100, a seat 200, a lens 300, a light source (LED) 400, a CMOS detector 500, two batteries 600, an ASIC transmitting module 700 and an antenna 800. With the diameter of a human small intestine around 25 mm, the capsule endoscope is able to squirm within the small intestine and capture images for detection. However, when entering the stomach, the capsule endoscope randomly moves around and cannot precisely observe specific portions of the stomach.

BRIEF SUMMARY OF INVENTION

An embodiment of an endoscope device of the invention comprises: a capsule sensor entering a human body for detection and sending out a signal; a driving device movably disposed outside of the human body to move and rotate the capsule sensor inside of the human body with non-contact force for omni-directionally human body detection; a data receiving device disposed outside of the human body which receives signals from the capsule sensor; and a power supply device providing power to the driving device and the data receiving device.

The capsule sensor comprises a housing which is capsule-shaped and has a periphery surface and two end surfaces and an inner magnetic element disposed in the housing. The driving device comprises a plurality of outer magnetic elements rotating around a first axis which attracts the inner magnetic element. When the driving device moves, the capsule sensor moves simultaneously and when the outer magnetic element rotates around the first axis, the capsule sensor rotates for omni-directionally detection.

When the outer magnetic element rotates at a low speed, the capsule sensor is rotated around a third axis extending through the inner magnetic element and perpendicular to a periphery surface.

The driving device further comprises: a turn table rotating around the first axis, wherein the outer magnetic elements are disposed on the turn table at equal distance with respect to the first axis; a base on which the turn table is disposed; and a cover covering the turn table and connected to the base maintaining rotation of the turn table when the driving device contacts the human body.

The driving device further comprises a motor disposed in the base and connected to the turn table to rotate the turn table, and a switch disposed on the base connecting the power supply device and the motor to start or stop the motor and control rotational speed of the turn table.

The detection module comprises at least one illuminating element disposed in the housing as a light source, at least one optical lens disposed in the housing to catch images of the human body, and at least one detecting element disposed in the housing to convert the images into signals.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIGS. 4e1 to 4h2 depict the magnetic field generated by the magnetic field control and data receiving device when the capsule sensor of the invention is rotated;

DETAILED DESCRIPTION OF INVENTION

An embodiment of an endoscope device of the invention comprises a capsule sensor, a driving device, a data receiving device and a power supply device. The capsule sensor can be swallowed by a patient to enter the alimentary canal. The driving device, the data receiving device and the power supply device are disposed outside of a human body. The capsule sensor is moved and rotated in the human body by the driving device to detect the alimentary canal omni-directionally. The detected image is converted into electronic signals which are transmitted to the data receiving device by wireless methods. The power for the capsule sensor is provided by a battery.

Figure 2:
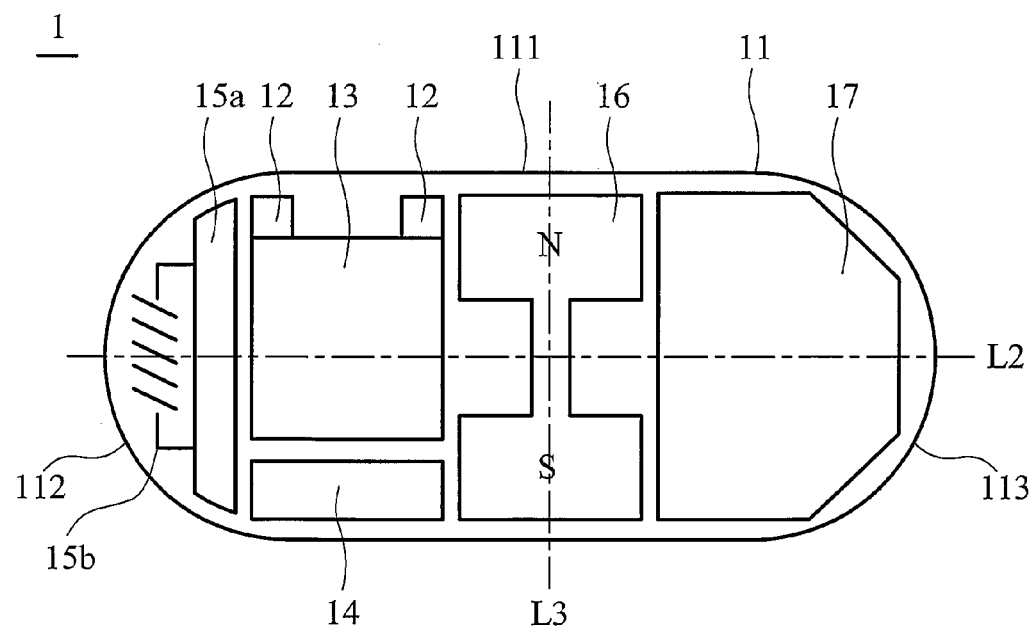
FIG. 2 is a schematic view of a capsule sensor of the invention.

Referring to FIG. 2, the capsule sensor 1 comprises a housing 11 having a capsule shape, a pair of illuminating elements 12, an optical lens 13, a detecting element 14, a first wireless module 15, a transmitter 15a, an antenna 15b, an inner magnetic element 16, and a battery 17.

The illuminating element 12 can be an LED, and the detecting element 14 can be a CMOS image sensor or a CCD image sensor.

The housing 11 has a cylinder periphery surface and two hemispherical end surfaces 112 and 113. The illuminating element 12 faces the periphery surface 111 and is electrically connected to the transmitter 15a to catch images. The detecting element 14 is electrically connected to the optical lens 13 and the transmitter 15a to convert the detected image to electronic signals. The transmitter 15a is disposed on the end surface 112 and is electrically connected to the antenna 15b to transmit electronic signals.

The inner magnetic element 16, which can be a permanent magnet, is disposed at the center of the housing 11. The magnetic poles of the permanent magnet are radically disposed with respect to a rotational axis (second axis) L2 of the housing 11 to provide magnetic force for spinning, moving or rotating. The battery 17 is disposed on the end surface 113 to provide power for all elements of the capsule sensor 1. The first wireless module 15 comprises an antenna 15b disposed on the end surface 112 to transmit signals to a second wireless module 21 of a magnetic field control and data receiving device 2.

Figures 3A, 3B:
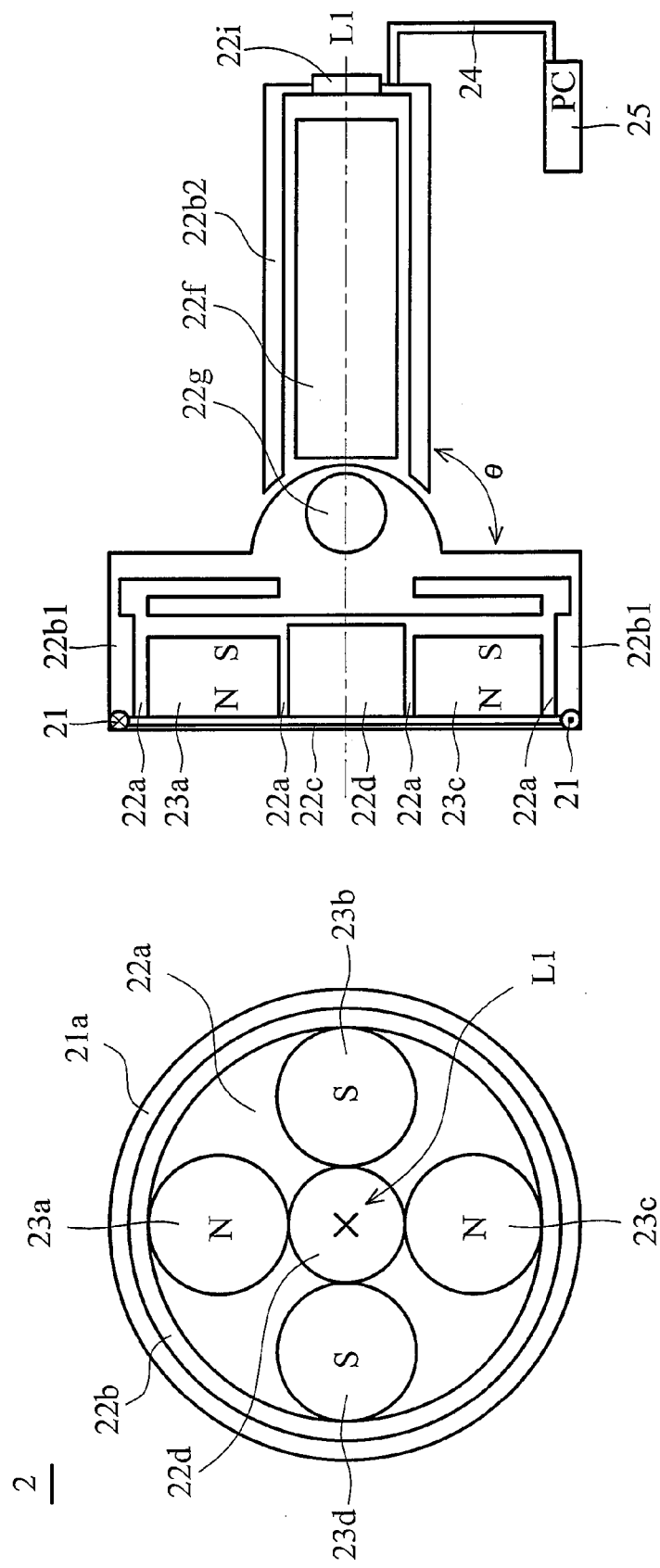
FIG. 3a is a front view of a magnetic field control and data receiving device of FIG. 2.
FIG. 3b is a side view of the magnetic field control and data receiving device of FIG. 2.

FIG. 3 depicts the driving device and data receiving device of the invention. In this embodiment, the driving device and the data receiving device are integrated as a magnetic field control and data receiving device. In this way, the data receiving device can move along with the driving device and receive signals from the capsule sensor 1. FIG. 3a is a front view of the magnetic field control and data receiving device 2, and FIG. 3b is a side view of the magnetic field control and data receiving device 2. The magnetic field control and data receiving device 2 comprises a second wireless module 21, a turn table 22a, a base 22b1, a handler 22b2, a cover 22c, a motor 22d, a data receiving and power supply module 22f, a shaft 22g, and four outer magnetic elements 23a~d.

In addition, the endoscope device of the invention further comprises a cable 24 and a work station 25.

The four outer magnetic elements 23a~d can be a permanent magnet or electric magnet.

The second wireless module 21 is disposed on the base 22b to receive the electronic signals from the first wireless module 21b of the capsule sensor 1 and connect to the data receiving and power supply module 22f.

The turn table 22a and the outer magnetic elements 23a~d generate a rotational magnetic field. The base 22b1 is connected to the second wireless module 21 and the cover 22c to constitute a housing of the magnetic field control and data receiving device 2. The handler 22b2 is jointed to the base 22b1 by the shaft 22g, whereby the angle θ between the handler 22b2 and the base 22b1 can be changed. The cover 22c covers the turn table 22a and contacts the human body, whereby the turn table 22a maintains rotation when the magnetic field control and data receiving device 2 contacts the human body. The motor 22d is disposed in the base 22b1. The shaft of the motor 22d is jointed to the turn table 22a to rotate the turn table 22. The data receiving and power supply module 22f is disposed in the handler 22b2 to provide power for the motor 22d and receive electronic signals from the second wireless module 21, which are transmitted from the first wireless module 15. A switch 22i is disposed on the bottom of the handler 22b2 and connected to the data receiving and power supply module 22f to start or stop the turn table 22a and control rotational speed of the turn table 22a. Four outer magnetic elements 23a~d surround an axis (first axis) L1 and are axially disposed on the turn table 22a with respect to the axis L1 to provide a magnetic field. The cable 24 is connected to the data receiving and power supply module 22f to transmit data to the work station 25 and provide power from the work station 25 to the data receiving and power supply module 22f.

Figure 4B:
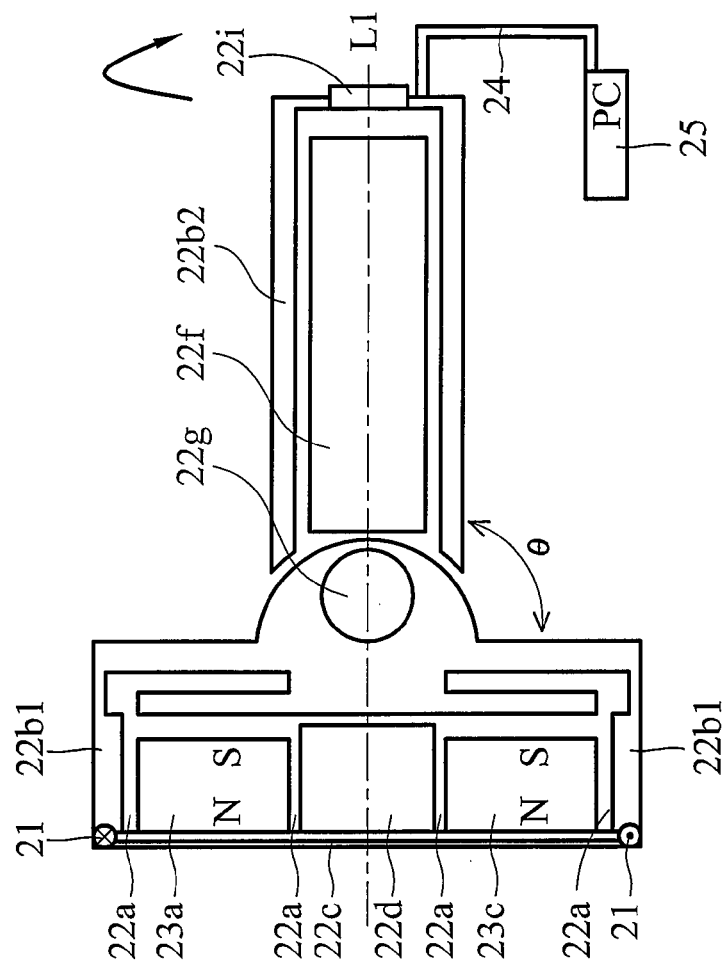
FIGS. 4a~4d depict the capsule sensor of the invention when applied to intestine detection.
Figure 4A:
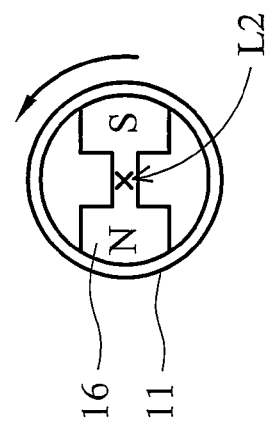
Figures 4C, 4D:
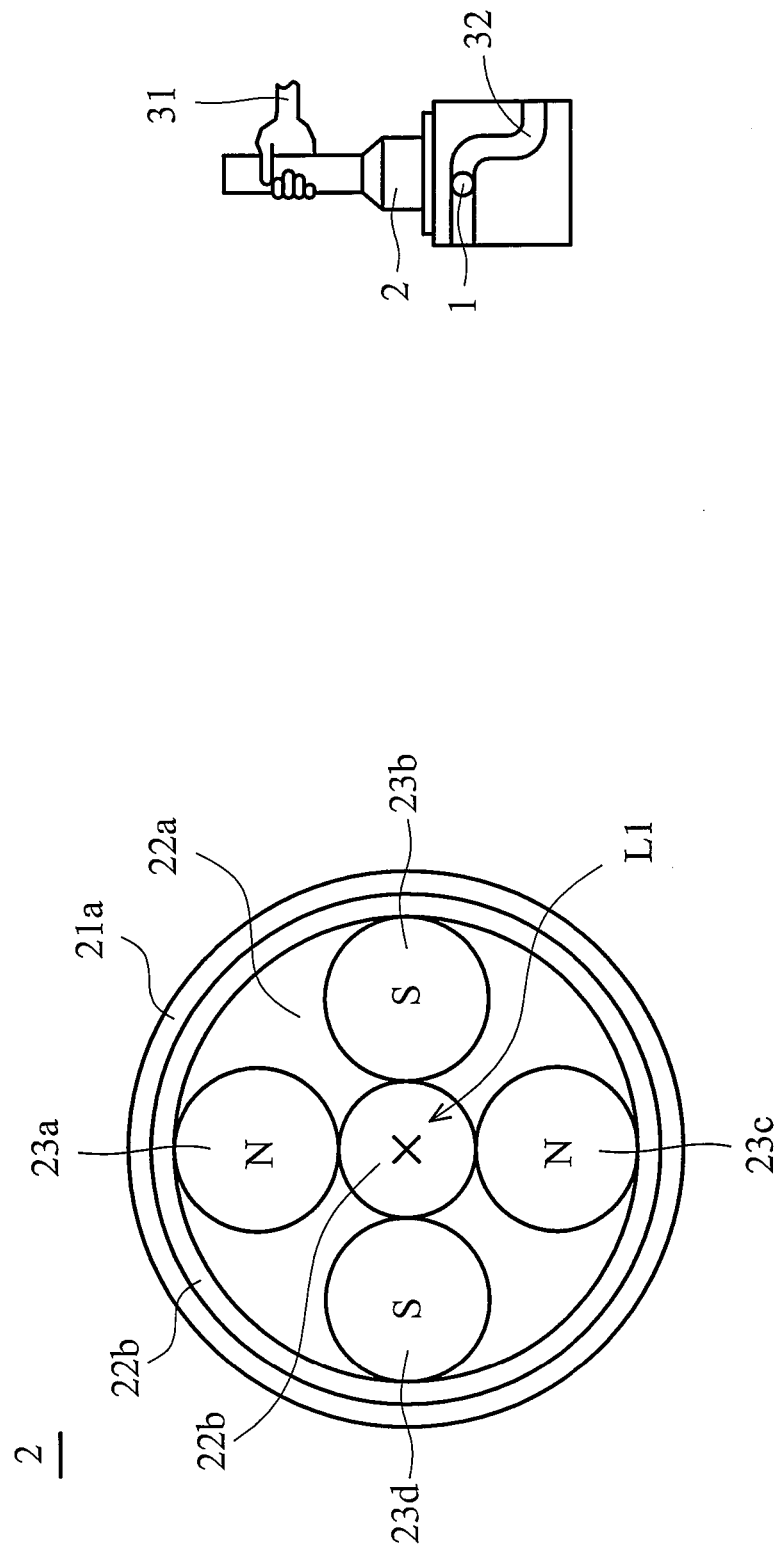

FIGS. 4a~4d depict the capsule sensor of the invention when applied to intestine detection. FIG. 4a is a cross section of the capsule sensor 1. FIG. 4b is a side view of the magnetic field control and data receiving device 2. FIG. 4c is a front view of the magnetic field control and data receiving device 2. FIG. 4d depicts a doctor using the endoscope device of the invention for intestine inspection. A doctor 31 holds the magnetic field control and data receiving device 2 to control the capsule sensor 1. The movement of the capsule sensor 1 is shown in FIGS. 4a, 4b and 4c. When the magnetic field control and data receiving device 2 is held in a specific position and the switch 22f is turned on, the motor 22d rotates the turn table 22a and the outer magnetic elements 23a~d which rotate the inner magnetic element 16 in the capsule sensor 1 to rotate the capsule sensor 1 around the axis L2, whereby the optical lens 13 on the end of the capsule sensor 1 captures views of different portions of an intestine. When the turn table 22a rotates, the capsule sensor 1 is capable of spinning whether the magnetic field control and data receiving device 2 moves or not.

The images caught by the optical lens 13 are converted into electronic signals by the detecting element 14. The electronic signals are processed in the transmitter 15a and transmitted to the second wireless module 21 via the antenna 15b of the first wireless module 15. The electronic signals are sent to the data receiving and power supply module 22f and further sent to the work station 25 via the cable 24.

The doctor 31 can manually move the magnetic field control and data receiving device 2 to move the capsule sensor 1 along the intestine 32 or stay at a position. When the magnetic field control and data receiving device 2 moves, the capsule sensor 1 is moved whether the turn table 22a rotates or not.

Figure 1:
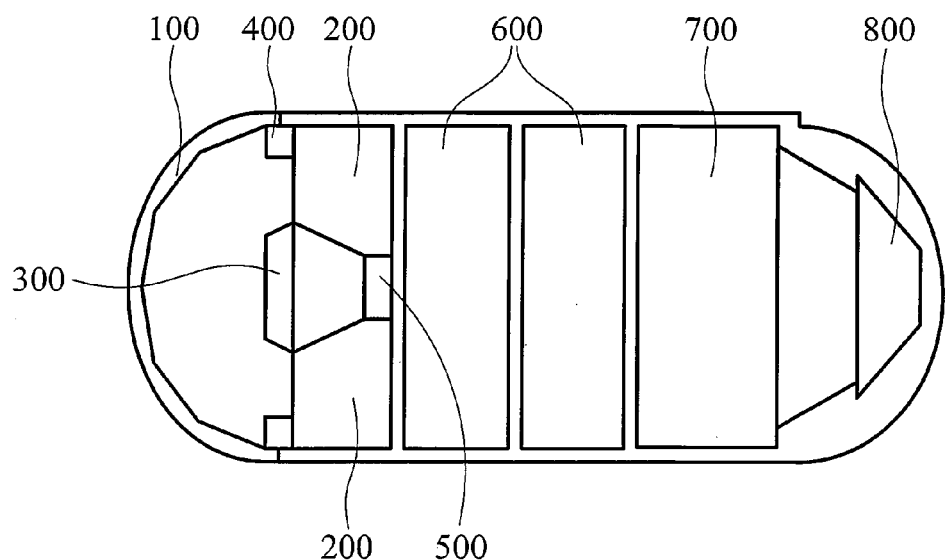
FIG. 1 is a schematic view of a conventional capsule endoscope device.

FIGS. 4e1 to 4h2 depict the magnetic field rotating the capsule sensor of the invention. When the turn table 22a starts, the outer magnetic elements 23a~23d are disposed as shown in FIG. 4e1. The capsule sensor 1 is disposed above the turn table 22a and located at the position marked by ▲. FIG. 4e2 is a side view observed from the position marked by ▲, wherein the magnetic field has an upward moving.

When the outer magnetic elements 23a~23d rotate to the arrangement shown in FIG. 4f1, the capsule sensor 1 still remains above the position marked by ▲. FIG. 4f2 is a side view observed from the position marked by ▲, wherein the magnetic field has a direction from left to right. Referring to the mark "T", compared with FIG. 4e2, the mark T moves from left to top in FIG. 4f2, which means the capsule sensor 1 spins 90°.

When the outer magnetic elements 23a~23d rotates to the arrangement shown in FIG. 4g1, the capsule sensor 1 still remains above the position marked by ▲. FIG. 4g2 is a side view observed from the position marked by ▲, wherein the magnetic field has a direction going downward. Compared with FIG. 4f2, the mark T moves from left to right in FIG. 4g2, which means the capsule sensor 1 spins 180°.

When the outer magnetic elements 23a~23d rotates to be the arrangement shown in FIG. 4h1, the capsule sensor 1 still remains above the position marked by ▲. FIG. 4h2 is a side view observed from the position marked by ▲, wherein the magnetic field has a direction from right to left. Compared with FIG. 4g2, the mark T moves from left to bottom in FIG. 4h2, which means the capsule sensor 1 spins 270°.

When the outer magnetic elements 23a~23d rotates back to be the arrangement shown in FIG. 4e1, the capsule sensor 1 still remains above the position marked by ▲. FIG. 4e2 is a side view observed from the position marked by ▲, wherein the magnetic field has a direction going upward. The mark T returns to left, which means the capsule sensor 1 spins 360°.

Figure 5C:
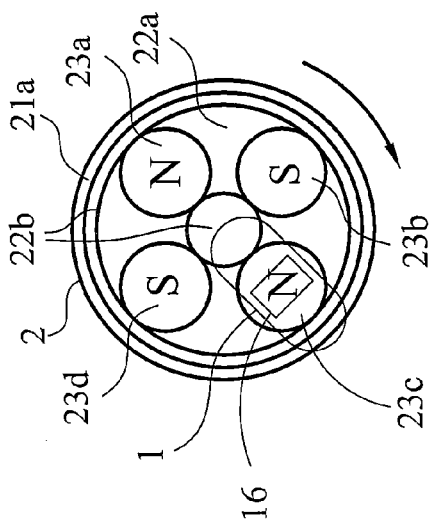
FIGS. 5a~5f depict the endoscope device of the invention when applied to stomach detection.
Figure 5F:
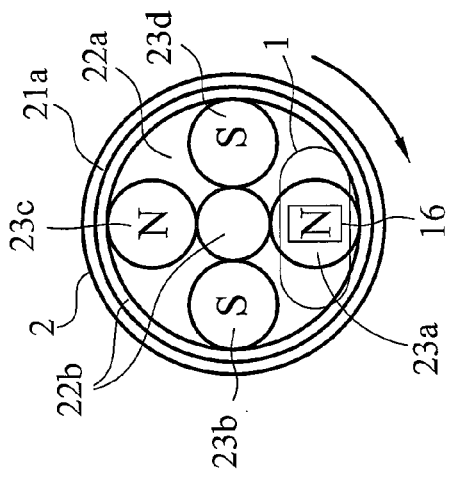
Figure 5B:
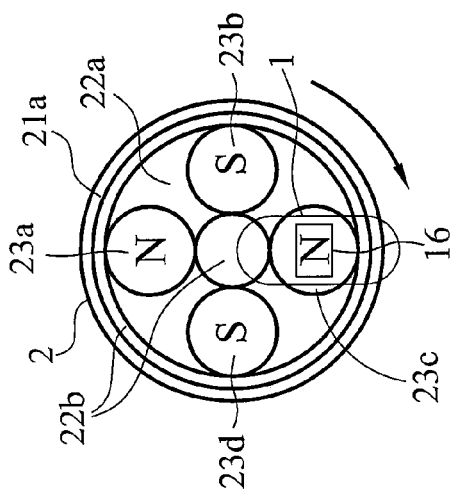
Figure 5E:
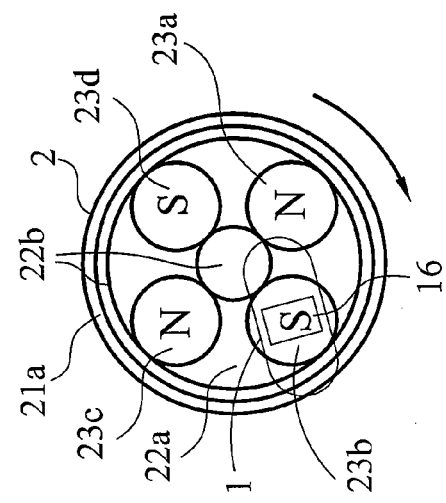
Figure 5A:
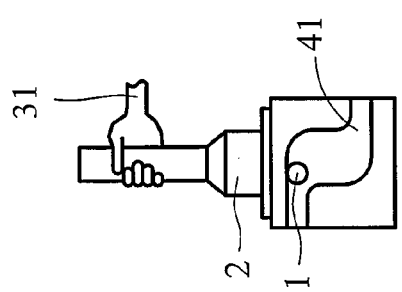
Figure 5D:
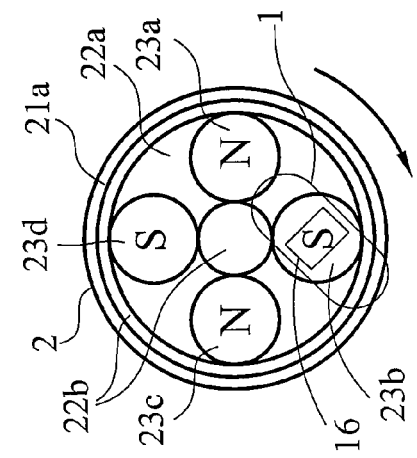

FIGS. 5a~5f depict the endoscope device of the invention detecting a stomach. FIG. 5a depicts a doctor operating the magnetic field control and data receiving device for stomach inspection. FIGS. 5b~5f depict the movement of the magnetic field control and data receiving device and the capsule sensor. A doctor 31 holds the magnetic field control and data receiving device 2 to control the capsule sensor 1. When the magnetic field control and data receiving device 2 remains in a position and the switch 22f is turned on to rotate the turn table 22 at a very low speed as shown in FIGS. 5b~5f, the slow rotation of the outer magnetic elements 23a~d rotates the capsule sensor 1 around another axis L3 (the third axis perpendicular to the periphery surface 111, see FIG. 2), whereby the optical lens 13 catches images of different portions of the stomach 41.

Figure 6:
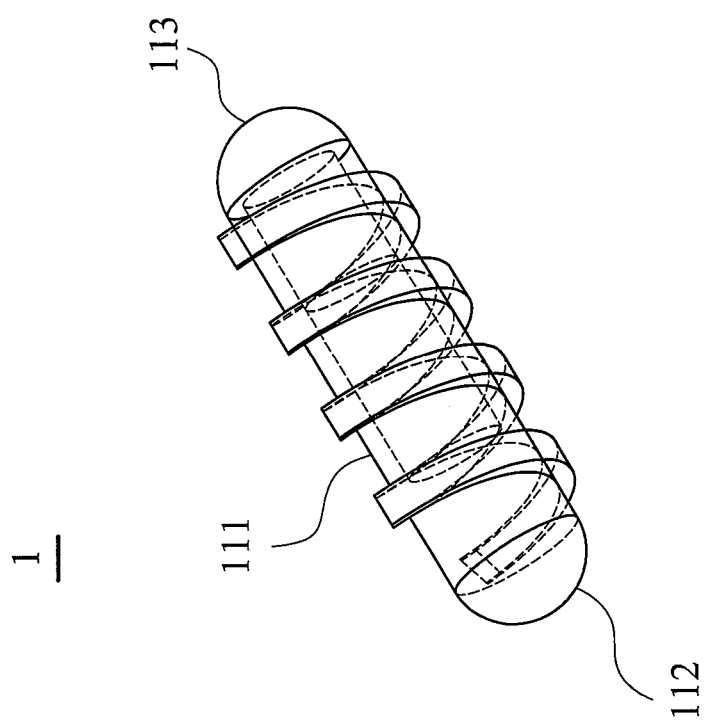
FIG. 6 is a perspective view of the capsule sensor of the invention.
Figure 7:
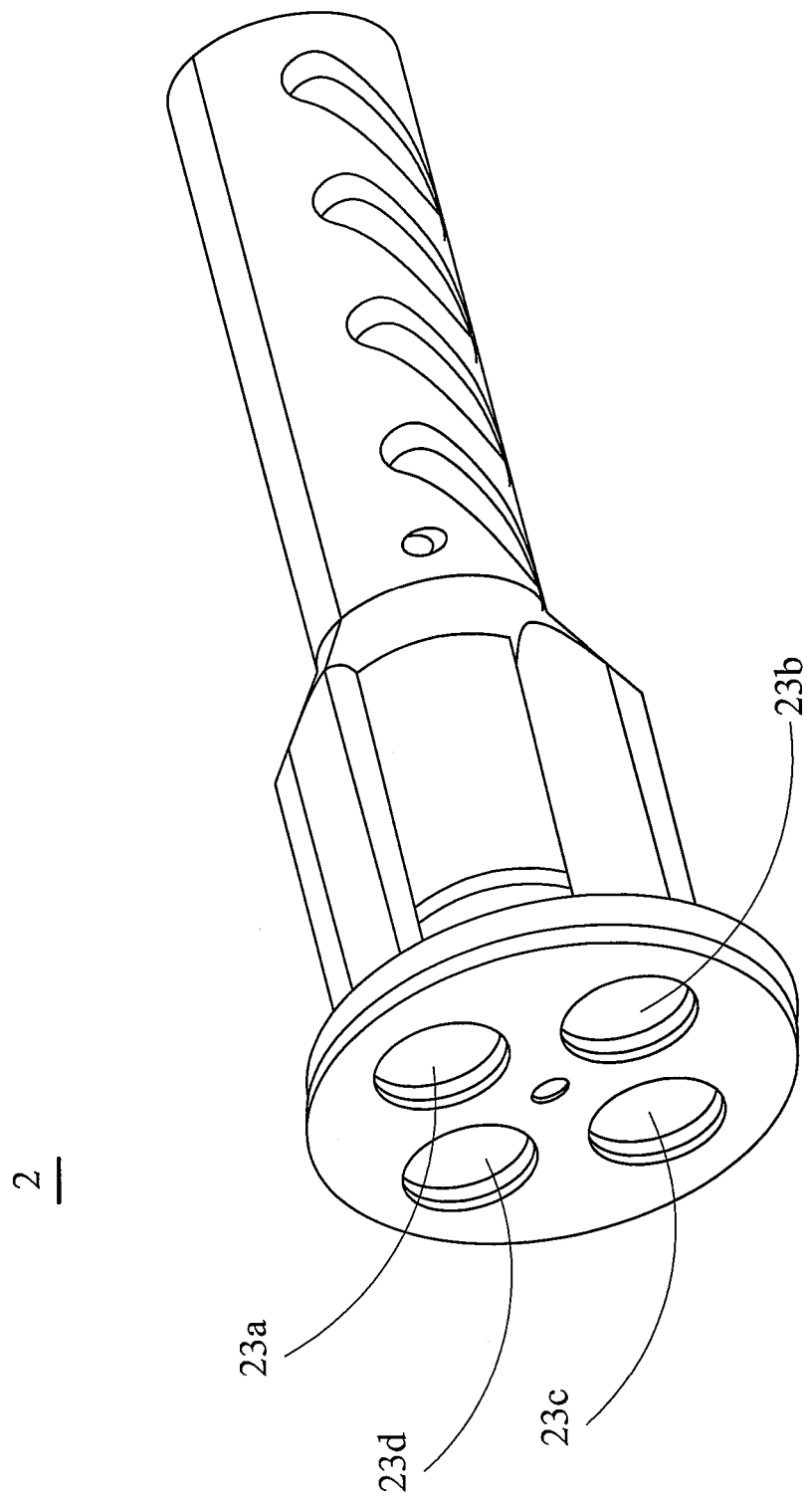
FIG. 7 is a perspective view of the magnetic field control and data receiving device of the invention.
Figure 8:
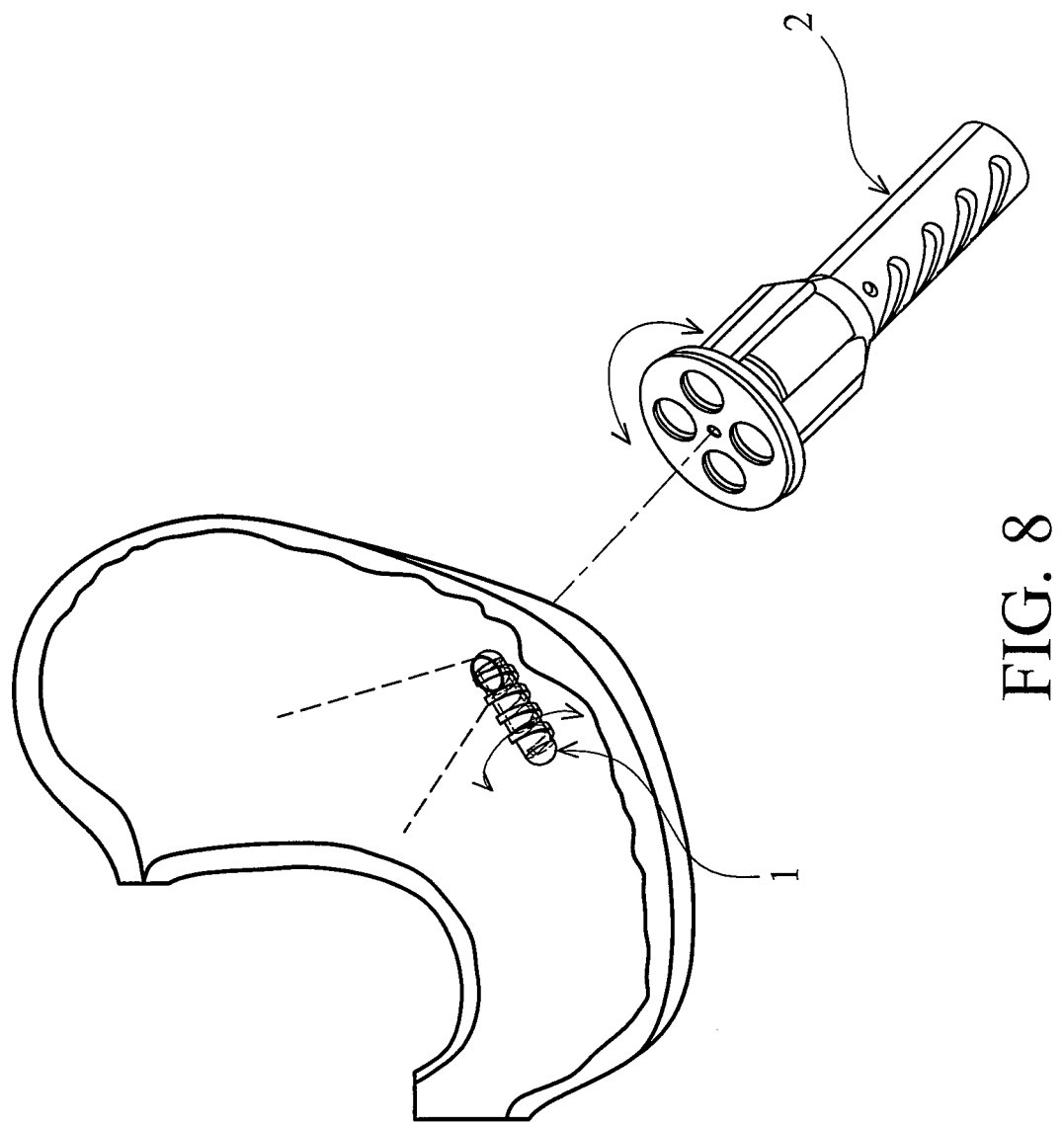
FIG. 8 depicts the magnetic field control and data receiving device controlling the capsule sensor when applied to stomach detection.

FIG. 6 is a perspective view of the capsule sensor of the invention. A screw portion is formed on the periphery surface 111 to stabilize the rotation of the capsule sensor 1. FIG. 7 is a perspective view of the magnetic field control and data receiving device. FIG. 8 depicts the magnetic field control and data receiving device 2 controlling the capsule sensor 1 to detect a stomach.

The invention also provides a magnetic field control method comprising the following steps.

The magnetic field control and data receiving device starts.

The capsule sensor catches images.

The caught images are converted into electronic signals transmitted from capsule sensor to the magnetic field control and data receiving device.

The magnetic field control and data receiving device is operated to move or rotate the capsule sensor.

In the last step, the rotation of the capsule sensor is controlled by the turn table of the magnetic field control and data receiving device whether the magnetic field control and data receiving device moves or not.

In the last step, the movement of the capsule sensor is controlled by the magnetic field control and data receiving device whether the turn table of the magnetic field control and data receiving device rotates or not.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A magnetic control method for an endoscope device comprising a capsule sensor and a driving device, comprising the following steps:
   providing a turn table and a plurality of outer magnetic elements disposed in the driving device wherein the turn table rotates around a first axis, and the outer magnetic elements are axially disposed with respect to the first axis so that the magnetic poles of the outer magnetic elements whose polarities are different are facing the turn table alternatively;
   providing an inner magnetic element disposed in the capsule sensor and radially disposed with respect to a second axis;
   attracting the inner magnetic element by the magnetic field generated by at least one of the outer magnetic elements;
   moving the capsule sensor by the movement of the driving device;
   rotating the outer magnetic elements around the first axis at a first speed to spin the capsule sensor around the second axis which is perpendicular to the first axis; and
   rotating the outer magnetic elements around the first axis at a second speed slower than the first speed to rotate the capsule sensor around a third axis which is parallel with the first axis.

2. The magnetic control method as claimed in claim 1, wherein in the step of rotating the outer magnetic elements around the first axis to spin the capsule sensor around the second axis, the spin angle of the capsule sensor is larger than the rotation angle of the turn table.

3. The magnetic control method as claimed in claim 1, wherein in the step of rotating the outer magnetic elements around the first axis to spin the capsule sensor around the second axis, the spin angle of the capsule sensor is twice the rotation angle of the turn table.

4. The magnetic control method as claimed in claim 1, wherein in the step of providing a turn table and a plurality of outer magnetic elements disposed in the driving device, the outer magnetic elements are separated from one another at equal distances.

5. The magnetic control method as claimed in claim 1, wherein the spinning of the capsule sensor is controlled by the driving device whether the driving device moves or not.

6. The magnetic control method as claimed in claim 1, wherein the rotation of the capsule sensor is controlled by the driving device whether the driving device moves or not.

7. The magnetic control method as claimed in claim 1, the movement of the capsule sensor is controlled by the driving device whether the turn table of the driving device rotates or not.

* * * * *